United States Patent [19]

Mimoun et al.

[11] Patent Number: 5,346,885
[45] Date of Patent: Sep. 13, 1994

[54] POLYCYCLIC COMPOUNDS AND THEIR USE AS PERFUMING INGREDIENTS

[75] Inventors: Hubert Mimoun, Challex, France; Francois Delay, Carouge; Philippe Schneider, Geneva, both of Switzerland

[73] Assignee: Firmenich S.A., Geneva, Switzerland

[21] Appl. No.: 94,658

[22] Filed: Jul. 20, 1993

[30] Foreign Application Priority Data

Jul. 22, 1992 [CH] Switzerland ............. 2307/92

[51] Int. Cl.$^5$ .............................................. A61K 7/46
[52] U.S. Cl. .................................. 512/15; 512/19; 560/256; 568/373
[58] Field of Search ............ 512/15, 19; 568/373; 560/256

[56] References Cited

U.S. PATENT DOCUMENTS

| | | | |
|---|---|---|---|
| 3,962,340 | 6/1976 | Nagakura et al. | 512/15 |
| 4,118,343 | 10/1978 | Skorianetz et al. | 512/15 |
| 4,142,997 | 3/1979 | Maurer | 568/373 |
| 4,311,852 | 1/1982 | Skorianetz et al. | 512/15 |
| 4,341,666 | 7/1982 | Skorianetz et al. | 512/15 |

FOREIGN PATENT DOCUMENTS 3501888  7/1986  Fed. Rep. of Germany ........ 512/19

OTHER PUBLICATIONS

F. Fringuelli et al., "Diels-Alder Reactions of Cycloalkenones, 16. Endo Diastereoselectivity of Some Cycloalkenones in Reactions With 1,3-Cyclohexadiene", J. Org. Chem. 54:3, pp. 710-712 (1989).

M. Nakazaki et al., "Synthesis and Chiroptical Properties of Optically Active C$_1$-Methanotwistane, C$_2$-Ditwistane, C$_1$-Homobasketane, and C$_2$-3,10-Dehydroditwistane", J. Org. Chem. 45:22, pp. 4440-4444 (1980).

K. Hirao et al., "Photo-reactivity of endo-Dicyclohexadiene (endo-1,4,4a,7,8,8a-Hexahydro-1,4-ethanonaphthalene)", J.C.S. Chem. Comm., pp. 577-578 (1977).

Primary Examiner—James H. Reamer
Attorney, Agent, or Firm—Pennie & Edmonds

[57]  ABSTRACT

The compounds of formula

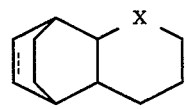

(Ia, b)

wherein symbol X designates a C=O (Ia) or C(CH$_3$)—OC(O)CH$_3$(Ib) group and the dotted line indicates the location of a single or double bond in formula (Ia) and of a double bond in formula (Ib), are characterised by useful odor notes of the aromatic, fruity, even amber type and can as a result be advantageously used as active perfuming ingredients.

8 Claims, No Drawings

POLYCYCLIC COMPOUNDS AND THEIR USE AS PERFUMING INGREDIENTS

BRIEF SUMMARY OF THE INVENTION

The present invention relates to the field of perfumery. More particularly, it concerns a method to confer, improve, enhance or modify the odor properties of a perfuming composition or a perfumed article, which method comprises adding to said composition or article a fragrance effective amount of a polycyclic ketonic compound of formula

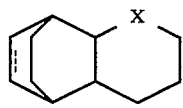

(Ia, b)

wherein symbol X designates a C=O (Ia) or C(CH$_3$)—OC(O)CH$_3$ (Ib) group and the dotted line indicates the location of a single or double bond in formula (Ia) and of a double bond in formula (Ib).

The invention also concerns novel 3-methyl-tricyclo[6.2.2.0$^{2,7}$]dodec-9-en-3-yl acetate and tricyclo[6.2.2.0$^{2,7}$]dodecan-3-one.

The invention further provides a perfuming composition or a perfumed article containing as an active perfuming ingredient a compound of formula (Ia,b) as defined above.

BACKGROUND OF THE INVENTION

Swiss patent n° 616 585 (owner: Firmenich SA) describes the use of tricyclo[6.2.1.0$^{2,7}$]undec-9-en-3-one as a perfuming or flavoring ingredient. Its odor properties are reminiscent of those of certain aromatic plants such as artemisia absynthium (wormwood) and liatris.

European patent EP 0 007 486 (owner: Firmenich SA) describes esters of formula

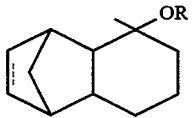

having a single or double bond in the position indicated by the dotted line and wherein symbol R represents a hydrogen atom or an acyl radical deriving from a saturated or unsaturated carboxylic add having from 1 to 6 carbon atoms. Amongst the compounds mentioned, there is 3-methyl-tricyclo[6.2.1.0$^{2,7}$]undec-9-en-3-yl acetate, which develops an original green odor note, characteristic of certain of the olfactive effects of clary sage. Although the compounds of the present invention have a structure close to that of the compounds described in the two cited patents, and are formally the higher homologues thereof, they possess odor properties which are distinct from those of said compounds and can, as a result find a use as original perfuming ingredients.

THE INVENTION

As is mentioned above the invention provides a method of use of compounds (Ia,b).

The two unsaturated compounds represented by formula (I) above are defined as being tricyclo[6.2.2.0$^{2,7}$]dodec-9-en-3-one and 3-methyl- tricyclo[6.2.2.0$^{2,7}$]dodec-9-en-3-yl acetate. The first of these compounds is a product already described in the scientific literature [see J. Org. Chem. 1989, 54, 710–2]. Its preparation has in fact been reported by Fringuelli et al. who investigated a whole series of compounds resulting from the Dieis-Alder reaction between the cyclohexenones and 1,3-cyclohexadiene. Their study prompted the authors to formulate certain theoretical considerations regarding the diastereoselectivity of this type of reaction. No particular mention or suggestion has however been made regarding any potential usefulness of the obtained tricyclic ketone. This same ketone has also been described by Hirao et al. [Chem. Comm. 1977, 577]and Nakazaki et al. [J. Org. Chem. 1980, 45, 4440–4444]. In both cases, and much like in the above-mentioned reference, there is strictly no mention of any usefulness of said ketone.

On the other hand, 3-methyl-tricyclo[6.2.2.0$^{2,7}$]dodec-9-en-3-yl acetate is a novel compound and as such it is an object of the present invention and the same applies to tricyclo[6.2.2.0$^{2,7}$]dodecan-3-one.

We have now discovered that, surprisingly, tricyclo[6.2.2.0$^{2,7}$]dodec-9-en-3-one develops an aromatic and fruity note, together with a green undernote. Its character is reminiscent of the odor of myrtle and artemisia, with its frankly thujonic side. It also possesses a floral character of the geranium type. When compared to its lower homologue, tricyclo[6.2.1.0$^{2,7}$]undec-9-en-3-one, the ketone of the invention possesses a far more pronounced aromatic side, while the floral note, which is totally absent from the odor of the undecenone, imposes itself as the dominant character. These olfactive characters render the tricyclo[6.2.2.0$^{2,7}$]dodec-9-en-3-one of the invention particularly adapted for the preparation of masculine compositions, as well as for use in technical perfumery. The saturated homologue of this ketone, i.e. tricyclo[6.2.2.0$^{2,7}$]dodecan-3-one, possesses a very natural aromatic, thujonic odor, more elegant and thujonic than that of the above-cited known undecenone, together with a myrtle and terpeneless cypress character.

As for 3-methyl-tricyclo[6.2.2.0$^{2,7}$]dodec-9-en-3-yl acetate, it presents the amber character which is typical of the ambergris headnote, without possessing the marine character. This note distinguishes it from its lower homologue, which presents a far more chemical aspect, almost benzoic, in the direction of Ylang. In practice, it was observed that the use of the acetate of the invention makes it possible to harmoniously complement the olfactive effect imparted by Ambrox (registered trademark of Firmenich SA), by giving to the compositions into which both ingredients are incorporated a distinct headnote which amplifies the groundnote characteristic of Ambrox ®.

Considering the above, it is not surprising to observe in practice that the compounds of the invention cannot be replaced by the prior art compounds. This fact illustrates once again the surprise character that, more often than not, surrounds the discoveries in the perfumery field. There are in fact many examples showing how an apparently minor modification in the molecular structure can bring about unexpected modifications, often fundamental, in the olfactive properties of a given compound. As a result, the man in the art does not dispose of any truly efficient criterion capable of guiding him in the choice that he must effect when synthesizing an active ingredient.

The polycyclic ketonic compounds of the invention can be used in concentrations which vary in a wide range of values. The perfumer knows by experience how to choose the appropriate proportions as a function of the nature of the other co-ingredients in a given composition and, of course, as a function of the olfactive character that he wants to achieve. Thus, proportions of the order of 5–10 to 40–50% can be used. Typically, such proportions can be inferior to these values when perfuming current consumer products such as soaps, detergents, hair-care products, cosmetics, body or air deodorants, or household products.

The compounds of the invention can be harmoniously combined with a great variety of other current perfuming ingredients both of natural and synthetic origin. To this effect, one can cite by way of example the compounds described in the reference book of S. Arctander, Perfume and Flavor Chemicals Montclair N.J. (USA) 1969. It goes without saying that the compounds of the invention can be used as such or, preferably, dissolved in a solvent or admixed with a current adjuvant beforehand.

As mentioned above, 3-methyl-tricyclo[6.2.2.0$^{2,7}$]dodec-9-en-3-yl acetate is a novel compound. It can be obtained from tricyclo[6.2.2.0$^{2,7}$]dodec-9-en-3-one by addition, under the conditions of a Grignard type reaction, of a methyl halomagnesium compound. The obtained carbinol, or 3-methyl-tricyclo[6.2.2.0$^{2,7}$]dodec-9-en-3-ol, can then be esterified via the usual techniques [see to this effect patent EP 0 007 486]. This process can be illustrated by the following reaction scheme:

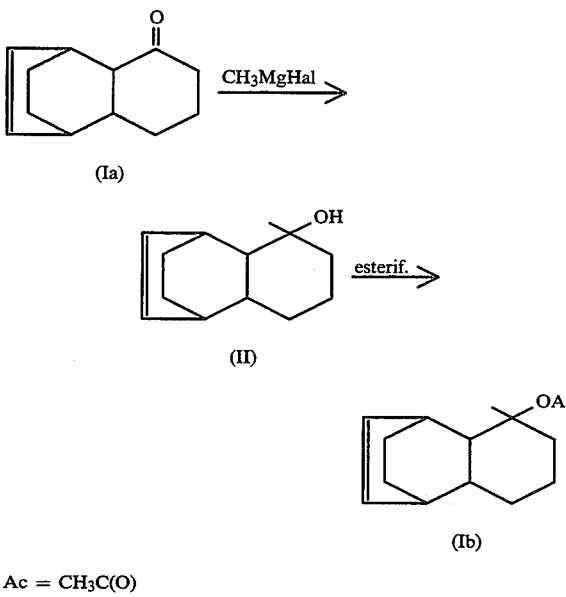

Ac = CH$_3$C(O)

The first step of the process can be easily carried out by means of methyl-magnesium chloride, bromide or iodide, while the esterification occurs via treatment of carbinol (II) with an acetylation agent of formula R-Y, wherein Y represents a halogen atom, for example chlorine or bromine, or a O-acetyl radical, and R represents an acetyl radical.

As is described in the literature [Fringuelli et al. op. cit.], ketone (Ia) can be prepared, following a Dieis-Alder type reaction, by adding cydohex-2-en-1-one onto cyclohexa-1,3-diene. Under the conditions mentioned (aluminium trichloride in toluene solution at 40° C.), the cycloaddition reaction shows a pronounced diastereoselectivity providing essentially the endo compound. However, whenever there is a reference in the present specification to compounds (Ia) and (Ib) as perfuming ingredients, it is meant to refer indifferently to the various possible configuration isomers, both endo- and exo-.

The saturated ketone (Ia) which, as indicated above, is a novel compound, can be prepared by catalytic hydrogenation of its unsaturated homologue above-cited. The hydrogenation conditions are described in detail in the examples presented hereinafter.

The invention is described in further detail by way of, but not limited to, the following examples wherein the temperatures are indicated in degrees centigrade and the abbreviations have the usual meaning in the art.

EXAMPLE 1

PREPARATION OF 3-METHYL-TRICYCLO[6.2.2.0$^{2,7}$]DODEC-9-EN-3-YL ACETATE a. 5.6 G (0.23 moles) of magnesium in chips and 16.6 g of tetrahydrofuran were introduced under nitrogen into a 4-neck reactor equipped with a mechanical stirrer, a thermometer, a condenser and an inlet funnel. A solution of methyl iodide 33 g (0.232 moles) in 100 ml of toluene was then added under stirring to the magnesium suspension while maintaining the temperature at about 40° by cooling externally. The reaction mixture was kept at this temperature during 20 min, then cooled down to 0° and 20.3 g of endo-tricyclo[6.2.2.0$^{2,7}$]dodec-9-en-3-one (0.115 moles) in 100 ml of toluene were added thereto. The rate of addition was adjusted so as to guaranty that the temperature of the reaction mixture would not go above 5°, then said temperature was allowed to increase to room temperature. After one night, the mixture was again cooled to 0° and the hydrolysis was carried out by controlled addition of 100 ml of a solution saturated with NH$_4$Cl. After decanting, the organic layer was separated. It was washed twice with water, dried over Na$_2$SO$_4$ and concentrated to yield a residue (29 g) which by distillation provided 18 g (yield 81%) of ($\pm$)-( 1RS,2SR,3RS,7RS)-3-methyl-tricyclo[6,2,2,0$^{2,7}$]dodec-9-en-3-ol.

B.p. 110°/0.5 hPa

MS: 192(M+,3), 174(11), 159(2), 149(6), 131(8), 112(10), 104(80(100), 67(7), 53(4), 43(18).

$^1$H-NMR: 1.25–1.74(m, 11H); 1.43(s, 3H); 2.01 (q, $^3$J=9, 1H); 2.05(s, 1H); 2.44(m, 1H); 2.72(m, 1H); 6.26 and 6.36(2t, $^3$J=7.2; 2H)δppm $^{13}$C-NMR: 16.0(t); 24.8(t); 25.1(t); 27.5(t); 29.9(d); 30.8(q); 34.3(t); 36.8(d); 41.0(d); 49.3(d); 72.0(s); 132.9(d); 135.4(d) δppm b. A mixture of 6.0 g (31.2 mmole) of the carbinol obtained under a. above, 60 ml of isopropenyl acetate and 0.025 g of p-toluenesulfonic acid was heated to reflux during 20 h. After cooling, the mixture was taken in ether, washed with a 5% aqueous solution of sodium bicarbonate, dried and concentrated. Bulb-to-bulb distillation (about 100°/0.05 hPa) gave 2.5 g (10.7 mmole; yield 34,2%) of ($\pm$)-(1RS,2SR,3RS,7RS)-3-methyl-tricyclo [6.2.2.0$^{2,7}$]dodec-9-en-3- yl acetate.

MS :234(M+,2), 219(1), 192(3), 174(33), 159(6), 146(18), 131(20), 122(17), 105(9), 94(100), 80(91), 67(8), 53(5), 43(45).

$^1$H-NMR: 1.20–1.58(m, 10H); 1.48(s, 3H); 1.93(s, 3H); 1.97(m, 1H); 2.36(m, 1H); 2.56(dd, $^3$J=8.5 and 12, 1H)); 2.62(m, 1H); 5.95 and 6.24(2t, $^3$J=7.5, 2H) δppm $^{13}$C-NMR: 18.2(t); 22.5(q); 23.8(t); 24.3(t); 24.7(q); 28.3(t); 30.7(t); 36.1(d); 40.7(d); 51.0(d); 82.3(s); 130.3(d); 134.3(d); 170.3(s) δppm

EXAMPLE 2

PREPARATION OF TRICYCLO[6.2.2.0$^{2,7}$]DODECAN-3-ONE

In a single-neck 100 ml flask, tricyclo[6.2.2.0$^{2,7}$]dodec-9-en-3-one (10 g, 56.81 mmole) was admixed with methanol (20 ml). There was then added 5% Pd/C (0.1 g) and the catalytic hydrogenation was carried out at atmospheric pressure during 1 h (stirring: 2000/rot/min). After filtration, concentration and bulb-to-bulb distillation (B.p. 120°/5hPa), 8.7 g (48.87 mmole) of the desired dodecanone were obtained (yield 86%).

IR(NaCl): 2940, 2860, 1695, 1460 cm$^{-1}$

MS: 178(M+,4), 160(1), 149(0.5), 110(3), 98(8), 97(100), 79(12), 67(6), 55(5), 41(9), 39(6).

$^{1}$H-NMR: 1.25–1.88(m, 12H); 1.90–2.60(m, 6H) δppm $^{13}$C-NMR: 20.46(t); 21.40(t); 21.62(t); 25.85(d); 26.00(t); 26.96(t); 27.42(t); 29.22(d); 39.01(d); 39.87(t) 49.88(d); 215.11(s) δppm

EXAMPLE 3

A base composition was prepared by admixing the following ingredients (parts by weight):

| Isobornyl acetate | 400 |
|---|---|
| Terpenyl acetate | 250 |
| Borneol cryst. | 50 |
| Camphene | 200 |
| Camphor | 700 |
| Caryolan$^{1)}$ | 100 |
| Coranol$^{2)}$ | 500 |
| Eucalyptol | 50 |
| Linalol | 1000 |
| Myrcene | 50 |
| 10%* trans-2-Hexenal | 100 |
| p-Cymene | 100 |
| Phellandrene | 50 |
| α-Pinene | 400 |
| Isobornyl propanoate | 200 |
| Orange terpenes | 400 |
| Terpinene | 200 |
| Terpineol | 100 |
| Terpinolene | 150 |
| p-Menthen-4-ol | 500 |
| Total | 5500 |

*in diethyl phthalate
$^{1)}$4,8-trimethyltricyclo[6.3.1.0$^{2,5}$]dodec-1-yl formiate; origin: Firmenich SA
$^{2)}$4-cyclohexyl-2-methyl-2-butenol; origin: Firmenich SA When 45 parts by weight of tricyclo[6.2.2.0$^{2,7}$]dodec-9-en-3-one were added to 55 parts by weight of the base composition described above, there was obtained a novel composition, the thujonic character of which was olfactively situated between artemisia and cedarleaf essential oil, while presenting a pleasant natural side.

When said dodecenone of the invention was replaced by an equivalent amount of tricyclo[6.2.1.0$^{2,7}$]undec-9-en-3-one (compound known from the prior art; see patent CH 616 585), there was obtained a composition whose character was much less terpenic-green, more aromatic and camphor, imparting to the composition a note of the rosemary and absinth type.

EXAMPLE 4

A composition intended for body deodorants was prepared by admixing the following ingredients (parts by weight):

| Benzyl acetate | 5 |
|---|---|
| Linalyl acetate | 25 |
| 10%* Methylnonyl-acetic ald. | 10 |
| Allyl amyl glycolate | 10 |
| Ambrox ® DL$^{1)}$ | 10 |
| Citral | 5 |
| Lemon ess. oil | 35 |
| Citronellol | 5 |
| Coumarine | 35 |
| Dihydromyrcenol$^{2)}$ | 90 |
| 10%* Estragol | 35 |
| Eugenol | 5 |
| Exaltolide ®$^{3)}$ | 25 |
| Hedione ®$^{4)}$ | 35 |
| 10%* Isobutylquinoleine | 5 |
| Lavandin ess. oil | 190 |
| Lilial ®$^{5)}$ | 45 |
| Lyral ®$^{6)}$ | 10 |
| Crystalmoss | 15 |
| Patchouli | 75 |
| Phenethylol | 5 |
| Amyl salicylate | 40 |
| Benzyl salicylate | 125 |
| Sandela ®$^{7)}$ | 75 |
| Vertofix coeur$^{8)}$ | 35 |
| Ylang synth. | 15 |
| 10%* Zestover$^{9)}$ | 15 |
| Total | 980 |

*in diethyl phthalate
$^{1)}$tetramethyl-perhydronaphtofuran; Firmenich SA
$^{2)}$International Flavors & Fragrances (IFF)
$^{3)}$pentadecanolide; Firmenich SA
$^{4)}$methyl dihydrojasmonate; Firmenich SA
$^{5)}$2-methyl-3-(4-tert-butyl-1-phenyl)-propanol; Givaudan-Roure
$^{6)}$4-(4-hydroxy-4-methylpentyl)-3-cyclohexene-1-carbaldehyde; IFF
$^{7)}$3-(5,5,6-trimethyl-bicyclo[2.2.1]hept-2-yl)-1-cyclohexanol; Givaudan-Roure
$^{8)}$International Flavors & Fragrances (IFF)
$^{9)}$2,4-dimethyl-3-cyclohexene-1-carbaldehyde; Firmenich SA When 2 parts by weight of 3-methyl-tricyclo[6.2.2.0$^{2,7}$]dodec-9-en-yl acetate were added to 98 parts by weight of the base composition above, there was obtained a novel composition whose amber note was clearly enhanced. The same applied to the lavandin character which became richer and more elegant.

EXAMPLE 5

A base composition intended for a masculine cologne was prepared by admixing the following ingredients (parts by weight):

| Benzyl acetate | 20 |
|---|---|
| Gaiol acetate | 30 |
| Geranyl acetate | 15 |
| Vetyveryl acetate | 15 |
| Anthranilol$^{1)}$ | 10 |
| Bergamot | 210 |
| 10%* Ceylan cinnamon | 20 |
| Citral | 25 |
| Lemon ess. oil | 100 |
| Citronellol | 10 |
| Civette | 20 |
| Coumarine | 15 |
| 10%* Cyclosal$^{2)}$ | 15 |
| 10%* Tarragon | 20 |
| Eugenol | 10 |
| Exaltolide ®$^{3)}$ | 20 |
| Geraniol | 5 |
| Bourbon geranium | 20 |
| Hydroxycitronellal | 15 |
| Iralia ®$^{4)}$ | 5 |
| Lavandin ess. oil | 35 |
| Linalol | 60 |
| Mandarin ess. oil | 15 |
| Oakmoss absolute | 20 |
| Musk C$^{5)}$ | 10 |
| Neroli Portugal | 15 |
| Oregano ess. oil | 5 |

| | |
|---|---:|
| Patchouli | 25 |
| AC product[6] | 90 |
| Sandalwood ess. oil. | 35 |
| Total | 910 |

*in diethyl phthalate
[1] methyl N-(7-hydroxy-3,7-dimethyl-1-octenyl)-anthranilate; Takasago
[2] 3-(4-isopropyl-1-phenyl)-2-methylpropanal; Firmenich SA
[3] pentadecanolide; Firmenich SA
[4] methyl-α-ionone; Firmenich SA
[5] 4-tert-butyl-3,5-dinitro-2,6-dimethyl-1-acetophenone
[6] 2,6,6,8-tetramethyl-tricyclo[5.3.1.0$^{1,5}$]undec-8-yl acetate; Givaudan-Roure When 9 parts by weight of 3-methyl-tricyclo[6.2.2.0$^{2,7}$]dodec-9-en-3-yl acetate were added to 91 parts by weight of the base composition above, the aromatic character of the latter was remarkably accentuated in a direction of the clary sage type. It turned out that said ester married perfectly to this essence. For example, addition to the base indicated of a mixture of 6 parts of acetate with 3 parts of clary sage oil made it possible to obtain a composition whose headnote had more impact and elegance than that observed when 9 parts of clary sage only were added to the same base composition.

What we claim is:

1. A method to confer, improve, enhance or modify the odor properties of a perfuming composition or a perfumed article, which method comprises adding to said composition or article a fragrance effective amount of a polycyclic ketonic compound of formula

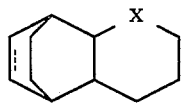
(Ia, b)

wherein symbol X designates a C=O (Ia) or C(CH$_3$)—OC(O)CH$_3$ (Ib) group and the dotted line indicates the location of a single or double bond in formula (Ia) and of a double bond in formula (Ib).

2. A method according to claim 1, wherein compounds (Ia, b) are present in their isomeric form of formula

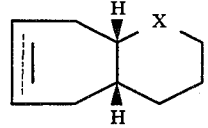

wherein X designates a C=O (Ia) or C(CH$_3$)—OC(O)CH$_3$ (Ib) group and the dotted line indicates the location of a single or double bond in formula (Ia) and of a double bond in formula (Ib).

3. A method according to claim 2, wherein the compound of formula (Ia,b) is (1RS, 2SR, 7RS)-tricyclo[6.2.2.0$^{2,7}$]dodec-9-en-3-one.

4. A method according to claim 2, wherein the compound of formula (Ia,b) is (1RS, 2SR, 3RS, 7RS)-3-methyl-tricyclo[6.2.2.0$^{2,7}$]dodec-9-en-3-yl acetate.

5. 3-Methyl-tricyclo[6.2.2.0$^{2,7}$]dodec-9-en-3-yl acetate.

6. Tricyclo[6.2.2.0$^{2,7}$]dodecan-3-one.

7. A perfuming composition or a perfumed article containing as an active perfuming ingredient a polycyclic ketonic compound of formula

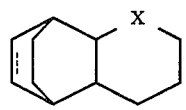
(Ia, b)

wherein symbol X designates a C=O (Ia) or C(CH$_3$)—OC(O)CH$_3$ (Ib) group and the dotted line indicates the location of a single or double bond in formula (Ia) and of a double bond in formula (Ib).

8. As a perfumed article according to claim 7, a soap, a detergent, a haircare product, a cosmetic preparation, a body or air deodorant or a household product.

* * * * *

UNITED STATES PATENT AND TRADEMARK OFFICE
CERTIFICATE OF CORRECTION

PATENT NO.   :   5,346,885

DATED        :   September 13, 1994

INVENTOR(S)  :   Mimoun et al.

It is certified that error appears in the above-identified patent and that said Letters Patent is hereby corrected as shown below:

Col. 8,
The formula for claim 2 should be:

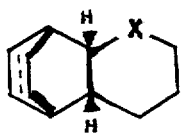

Signed and Sealed this

Tenth Day of January, 1995

Attest:

BRUCE LEHMAN

Attesting Officer

Commissioner of Patents and Trademarks